United States Patent [19]

Johnson et al.

[11] Patent Number: 4,529,732
[45] Date of Patent: Jul. 16, 1985

[54] 2-[2-HYDROXY-4-(SUBSTITUTED)PHENYL]-PIPERIDINES

[75] Inventors: Michael R. Johnson, Gales Ferry; Lawrence S. Melvin, Jr., Ledyard, both of Conn.

[73] Assignee: Pfizer Inc., New York, N.Y.

[21] Appl. No.: 474,957

[22] Filed: Mar. 14, 1983

[51] Int. Cl.³ ............... A61K 31/445; C07D 211/46
[52] U.S. Cl. ..................... 514/327; 546/221; 546/216; 546/187; 546/188; 546/194; 546/208; 546/226; 546/232; 546/233; 546/235; 546/237; 546/238; 546/240; 514/867
[58] Field of Search ............... 546/221, 240; 424/267

[56] References Cited

U.S. PATENT DOCUMENTS

| | | | |
|---|---|---|---|
| 2,498,431 | 2/1950 | Lee | 546/240 |
| 4,147,872 | 4/1979 | Althuis et al. | 546/216 |
| 4,216,218 | 8/1980 | Klioze et al. | 546/221 |
| 4,306,097 | 12/1981 | Harbert et al. | 568/731 |

Primary Examiner—Norma S. Milestone
Attorney, Agent, or Firm—Charles J. Knuth; Albert E. Frost; Paul D. Thomas

[57] ABSTRACT

2-[2-Hydroxy-4-(substituted)phenyl]piperidines and derivatives thereof of the formula

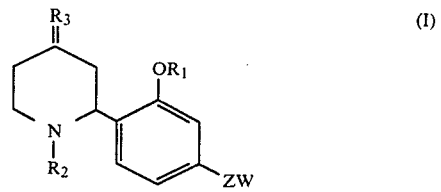

or a pharmaceutically acceptable acid addition salt thereof, wherein $R_1$ is H, benzyl or certain acyl groups, $R_2$ is H, certain alkyl, alkenyl, alkynyl, hydroxyalkyl, acyl or alkylsulfonyl groups; $R_3$ is $H_2$, O,

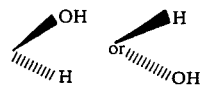

and Z is $(C_1-C_{13})$alkylene or $-(alk_1)_m-O-(alk_2)_n-$ where each of $(alk_1)$ and $(alk_2)$ is $(C_1-C_{13})$alkylene, provided that the number of carbon atoms in $(alk_1)$ plus $(alk_2)$ is not greater than 13; each of m and n is 0 or 1; and W is H, pyridyl or optionally substituted phenyl; their use as analgesic agents, intermediates therefor and processes for their preparation.

5 Claims, No Drawings

2-[2-HYDROXY-4-(SUBSTITUTED)PHENYL]-PIPERIDINES

BACKGROUND OF THE INVENTION

1. Field of the Invention

The invention relates to certain 2-phenylpiperidine compounds, more particularly to certain 2-[2-hydroxy-4-(ZW-substituted)phenyl]piperidines of the formula

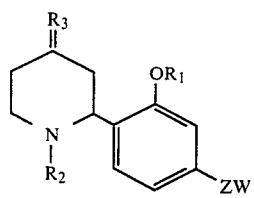

or a pharmaceutically acceptable acid addition salt thereof, useful as CNS agents, especially as analgesics, antiemetic and antidiarrheal agents for use in mammals, including man, methods for their pharmaceutical compositions containing them and intermediates therefore.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesics such as d-propoxyphene, codeine, and morphine, possess addictive liability. The need for improved and potent analgesics is, therefore, evident.

More recently, great interest in cannabinol-type compounds as analgesic agents has been exhibited, see, for example, R. Mechoulam, Ed., "Marijuana Chemistry, Pharmacology, Metabolism and Clinical Effects", Academic Press, New York, N.Y., 1973; Mechoulam, et al., *Chemical Reviews*, 76, 75–112 (1976).

U.S. Pat. No. 4,147,872, issued Apr. 23, 1979, discloses a series of 3-[2-hydroxy-4-(substituted)phenyl]-piperidine CNS agents of the formula

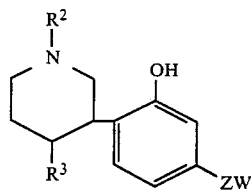

where $R^2$ and $R^3$ have certain values in common with $R_2$ and $R_3$, respectively, as defined for the instant compounds of formula (I). The compounds of formula (II) are active analgesics, tranquilizers, sedatives and antianxiety agents for use in mammals, and/or as anticonvulsants, diuretics and antidiarrheal agents.

U.S. Pat. No. 4,306,097, issued Dec. 15, 1981, discloses 3-[2-hydroxy-4-(substituted)phenyl]cycloalkanol analgesic agents.

SUMMARY OF THE INVENTION

It has now been found that certain 2-[2-hydroxy-4-(substituted)phenyl]piperidines and derivatives thereof are effective CNS agents, especially as analgesics, tranquilizers, sedatives and antianxiety agents in mammals, including humans and/or anticonvulsants, diuretics and antidiarrheal agents in mammals, including man. They are especially effective in said mammals as analgesics, antidiarrheals and as agents for treatment and prevention of emesis and nausea, especially that induced by antineoplastic drugs. Said invention compounds, which are nonnarcotic and free of addiction liability, are of the formula

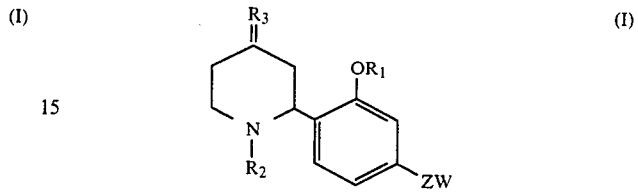

or a pharmaceutically acceptable acid addition salt thereof, wherein $R_1$ is H, benzyl, benzoyl, formyl, $(C_2-C_7)$alkanoyl or $CO(CH_2)_pNR_4R_5$ where p is zero or is 1–4 and $R_4$ and $R_5$ are each H or $(C_1-C_4)$alkyl or taken together with the nitrogen atom to which they are attached, they form a piperidino, pyrrolo, pyrrolidino, morpholino or N-[$(C_1-C_4)$alkyl]-piperazino group;

$R_2$ is H, formyl, $(C_1-C_6)$alkyl, $(C_2-C_6)$alkenyl, $(C_2-C_6)$alkynyl, $(C_2-C_7)$hydroxyalkyl, $(C_2-C_7)$alkylcarbonyl, $(C_3-C_7)$alkenylcarbonyl, $(C_3-C_7)$alkynylcarbonyl, $(C_1-C_6)$alkylsulfonyl, $(C_2-C_7)$alkoxycarbonyl or $(C_2-C_7)$hydroxyalkylcarbonyl;

$R_3$ is two atoms of hydrogen, a carbonyl oxygen atom,

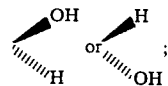

Z is $(C_1-C_{13})$alkylene or -(alk$_1$)$_m$-O-(alk$_2$)$_n$- where each of (alk$_1$) and (alk$_2$) is $(C_1-C_{13})$alkylene with the proviso that the sum of carbon atoms in (alk$_1$) plus (alk$_2$) is not greater than 13, and each of m and n is 0 or 1; and W is hydrogen, pyridyl or $W_1C_6H_4$ where $W_1$ is H, F or Cl.

Particularly preferred compounds of formula (I) are those wherein:

$R_1$ is hydrogen or alkanoyl, especially hydrogen or acetyl;

$R_2$ is $(C_1-C_6)$alkyl, $(C_2-C_6)$alkenyl, $(C_2-C_6)$alkynyl, $(C_2-C_7)$alkylcarbonyl, $(C_2-C_7)$alkoxycarbonyl or $(C_1-C_6)$alkylsulfonyl, especially n-propyl, 2-propenyl, 2-propynyl, $(C_2-C_5)$alkylcarbonyl or $(C_2-C_4)$alkoxycarbonyl;

$R_3$ is

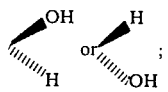

Z is said alkylene or O(alk$_2$); and

W is hydrogen or phenyl;

especially preferred ZW are $C(CH_3)_2(CH_2)_5CH_3$ or $OCH(CH_3)(CH_2)_3C_6H_5$.

More particularly preferred compounds of the invention because of their enhanced biological activity relative to other compounds described herein are the cis isomers of the formula

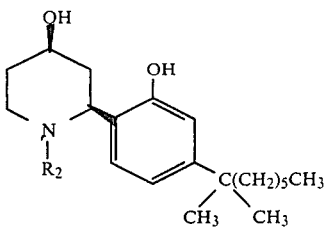

where $R_2$ is as shown in the table.

$R_2$ $CH_2CH_2CH_3$
$CH_2CH=CH_2$
$CH_2C\equiv CH$
$CO_2CH_3$
$CO_2CH_2CH_3$
$SO_2CH_3$
$COCH_3$
$COCH_2CH_3$
$COCH_2CH_2CH_3$
$CO(CH_2)_3CH_3$ Most particularly preferred such compounds are N-butyryl cis-2-[4-(1,1-dimethylheptyl)-2-hydroxyphenyl]-4-piperidinol and N-ethoxycarbonyl cis-2-[4-(1,1-dimethylheptyl)-2-hydroxyphenyl]-4-piperidinol.

More particularly preferred compounds of the invention which are useful as intermediates in preparation of the above biologically active compounds, are of the formula

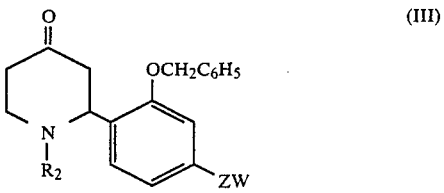

(III)

where $R_2$ and ZW are as previously defined. Especially preferred such intermediates are those wherein $R_2$ is $COOCH_3$ or $COOC_2H_5$ and ZW is $C(CH_3)_2(CH_2)_5CH_3$ or $OCH(CH_3)(CH_2)_3C_6H_5$.

Also included in the present invention are the pharmaceutically acceptable acid addition salts of the compounds of formula (I) which contain a basic group. In compounds having two or more basic groups present, such as those wherein W is pyridyl and/or $R_1$ represents a basic ester moiety, polyacid addition salts are possible. Representative of such pharmaceutically acceptable acid addition salts are the mineral acid salts such as the hydrochloride, hydrobromide, sulfate, phosphate, nitrate; organic acid salts such as the citrate, acetate, sulfosalicylate, tartrate, glycolate, malate, malonate, maleate, pamoate, salicylate, stearate, phthalate, succinate, gluconate, 2-hydroxy-3-napthoate, lactate, mandelate and methanesulfonate.

Compounds of formula (I) contain an asymmetric center at the 2-position and, when $R_3$ is a secondary alcohol group, at the 4-position. They may contain additional centers of asymmetry in the $R_1$, $R_2$ and ZW substituents. For convenience, the above formulae depict the racemic compounds. However, the above formulae are considered to be generic and embracive of racemic modifications of the compounds of the invention, the diastereomeric mixtures, the pure enantiomers and diastereomers thereof. The utility of the racemic mixture, the diastereomeric mixture as well as the pure enantiomers and diastereomers is determined by the biological evaluation procedures described below.

As mentioned above, the compounds of the invention are particularly useful as analgesics, antidiarrheals and as antiemetic and antinausea agents for use in mammals, including man. The invention further provides a method for producing analgesia in mammals and a method for prevention and treatment of nausea in a mammal subject to nausea, in each case by oral or parenteral administration of an effective amount of a compound of formula (I) or a pharmaceutically acceptable salt.

Also provided are pharmaceutical compositions for use as analgesics, as well as those suitable for use in prevention and treatment of nausea, comprising an effective amount of compound of the invention and a pharmaceutically acceptable carrier.

DETAILED DESCRIPTION OF THE INVENTION

The compounds of this invention having formula (I) wherein $R_3$ is a carbonyl oxygen atom are prepared from the appropriate hydroxy-protected 2-bromo 5-(ZW substituted)phenol. Suitable hydroxy protecting groups are those which do not interfere with subsequent reactions and which can be removed under conditions which do not cause undesired reactions at other sites of said compounds or of products produced therefrom. Representative of such protective groups are methyl, ethyl, benzyl or substituted benzyl wherein the substituent is, for example, alkyl having from one to four carbon atoms, halo (Cl, Br, F, I) and alkoxy having from one to four carbon atoms.

The exact chemical structure of the protecting group is not critical to this invention since its importance resides in its ability to perform in the manner described above. The selection and identification of appropriate protecting groups can easily and readily be made by one skilled in the art. The suitability and effectiveness of a group as a hydroxy protecting group are determined by employing such a group in the herein-illustrated reaction sequences. It should, therefore, be a group which is easily removed to regenerate the hydroxy groups. The benzyl group is a preferred group since it can be removed by catalytic hydrogenolysis or acid hydrolysis.

Detailed procedures for preparing the hydroxy-protected 2-bromo-5(ZW-substituted)phenol starting materials, including those of formula (V) wherein the hydroxy-protecting group is benzyl, are described in U.S. Pat. Nos. 4,147,872 and 4,306,097 each of which are hereby incorporated herein by reference.

The protected 2-bromo-5-(ZW-substituted)phenol (V) is subjected to a copper catalyzed Grignard reaction in a reaction-inert solvent with the appropriate N-$R_2$-substituted-4-oxo-1,2,3,4-tetrahydropyridine (IV) as shown in Scheme A for the preferred case where the hydroxy protecting group is benzyl. Suitable reaction-inert solvents are cyclic and acyclic ethers such as, for example, tetrahydrofuran, dioxane, diethyl ether and ethylene glycol dimethyl ether.

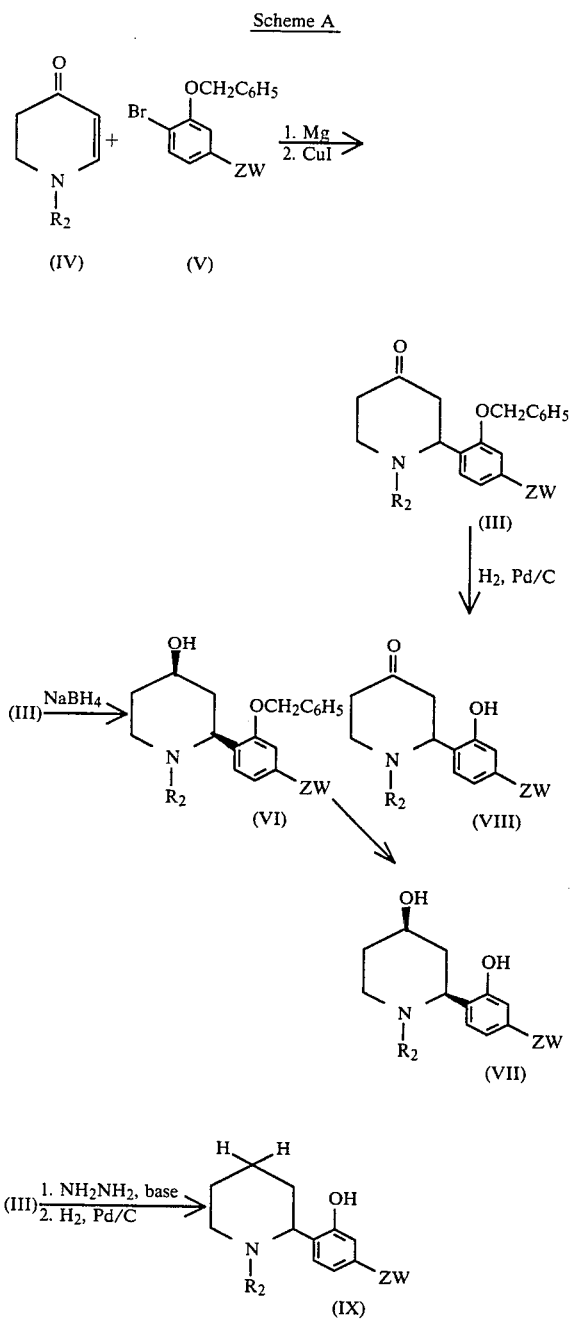

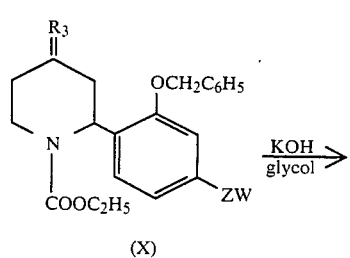

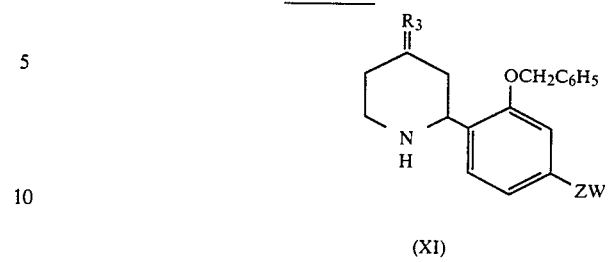

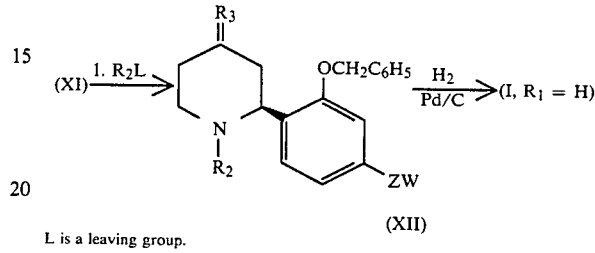

L is a leaving group.

The Grignard reagent is formed in known manner, as, for example, by refluxing a mixture of one molar proportion of the bromo reactant and two molar proportions of magnesium in a reaction-inert solvent, e.g., tetrahydrofuran at reflux temperature. The resulting mixture is then cooled to about −20° to 25° C. and a cuprous salt, for example, cuprous iodide or cuprous bromide, added in a catalytic amount. The appropriate 4-oxo-1,2,3,4-tetrahydropyridine[2,3-dihydro-4-(1H)pyridinone (IV)] is then added at a temperature of from about −20° to 0° C.

The product of the Grignard reaction of formula (III) can then be treated with an appropriate reagent to remove the protecting group. If desired, the benzyl group on the phenolic hydroxy group is conveniently removed by catalytic hydrogenation over palladium-on-carbon. Alternatively, the phenolic benzyl group can be removed by acid hydrolysis using, for example, trifluoroacetic acid.

The preferred intermediate (III) can also be reacted under reducing conditions known to convert ketones to secondary alcohol groups. For example, catalytic hydrogenation over a noble metal catalyst, for example, platinum, palladium or nickel; or reduction with an alkali metal hydride, for example, lithium aluminum hydride, sodium borohydride, potassium borohydride. A preferred reducing agent for this conversion is sodium borohydride because it gives rise to a predominantly di-cis-product (VI). The reaction is carried out in a polar solvent, for example, a lower alcohol such as methanol, ethanol or 2-propanol; water, an ether such as diethyl ether, tetrahydrofuran, diglyme or mixtures thereof; and at a temperature of from about −70° C. up to the reflux temperature of the solvent. An especially preferred temperature is in the range of from −50° to 25° C., at which temperature the reaction is substantially complete in a few hours. The resulting 4-piperidinol is separated by known methods and purified, if desired, for example, by silica gel column chromatography.

Alternatively, the intermediate ketones of formula (III) can be reduced to the corresponding piperidine derivatives of formula (IX) by methods known to reduce ketones to hydrocarbons. Examples of such methods are the well known Clemmensen method employing amalgamated zinc and hydrochloric acid (see e.g., "Organic Reactions", Academic Press, New York, Vol. 1, 1942, page 155) and the Wolff-Kishner reduction employing hydrazine and a strong base such as potassium hydroxide [see, e.g., "Organic Reactions", Vol. 4, page 378 (1948)]. A particularly preferred method is the Wolff-Kishner reduction employing hydrazine hydrate and potassium hydroxide in ethylene glycol as solvent. A preferred temperature for this reaction is from 50° to 250° C., especially 100°–200° C., at which temperature the reaction is complete within a few hours. The benzyl ether of the 2-phenylpiperidine compound of formula (IX) is then isolated by methods well known in the art and the benzyl group removed by methods described above.

As mentioned above, the benzyl hydroxy-protecting group such as that present in the above compounds of formulae (III) or (VI), for example, are preferably removed by catalytic hydrogenolysis. The hydrogenolysis of such compounds is ordinarily carried out by means of hydrogen in the presence of a noble metal catalyst. Examples of noble metals which may be employed are nickel, palladium, platinum and rhodium. The catalyst is ordinarily employed in catalytic amounts, e.g., from about 0.01 to 10 weight-percent and preferably from about 0.1 to 2.5 weight-percent, based on the starting compound, e.g. the benzyl ether (III) or (VI). It is often convenient to suspend the catalyst on an inert support, a particularly preferred catalyst is palladium suspended on an inert support such as carbon.

One convenient method of carrying out this transformation is to stir or shake a solution of the starting compound, e.g. (III) or (VI), under an atmosphere of hydrogen in the presence of one of the above noble metal catalysts. Suitable solvents for this hydrogenolysis reaction are those which substantially dissolve the starting compound but which do not themselves suffer hydrogenation or hydrogenolysis. Examples of such solvents include the lower alkanols such as methanol, ethanol and isopropanol; ethers such as diethyl ether, tetrahydrofuran, dioxane and 1,2-dimethoxyethane; low molecular weight esters such as ethyl acetate and butyl acetate; tertiary amides such as N,N-dimethylformamide, N,N-dimethylacetamide and N-methylpyrrolidone; and mixtures thereof. Introduction of the hydrogen gas into the reaction medium is usually accomplished by carrying out the reaction in a sealed vessel, containing the starting compound, the solvent, the catalyst and the hydrogen. The pressure inside the reaction vessel can vary from about 1 to about 100 kg/cm$^2$. The preferred pressure range, when the atmosphere inside the reaction vessel is substantially pure hydrogen, is from about 2 to about 5 kg/cm$^2$. The hydrogenolysis is generally run at a temperature of from about 0° to about 60° C., and preferably from about 25° to about 50° C. Utilizing the preferred temperature and pressure values, hydrogenolysis generally takes place in a few hours, e.g., from about 2 hours to about 24 hours.

The product is then isolated by standard methods known in the art, e.g., filtration to remove the catalyst and evaporation of solvent or partitioning between water and a water immiscible solvent and evaporation of the dried extract.

As illustrated in Scheme B, above, an N-alkoxycarbonyl intermediate of formula (X) can be subjected to hydrolysis and decarboxylation to provide the corresponding base of formula (XI). The free base can then be alkylated or acylated by reaction with a compound of formula $R_2L$ wherein $R_2$ may have any of the values given above, but preferably is not H, and L is a leaving group, to provide the corresponding compound of formula (VI).

The hydrolysis and decarboxylation of the N-alkoxycarbonyl compounds such as the N-ethoxycarbonyl compound of formula (X) is carried out in an aqueous solvent, and a strong base. Preferred solvents for this conversion are a lower alcohol, e.g., methanol, ethanol or isopropanol; a glycol such as ethylene glycol or diethylene glycol, water or mixtures thereof. Preferred as strong base for the hydrolysis are potassium hydroxide, sodium hydroxide, calcium hydroxide or potassium carbonate. In an especially preferred such method the N-ethoxycarbonyl compound of formula (X) in ethanol is added to ethylene glycol containing a molar excess of potassium hydroxide and water. The mixture is evaporated to remove alcohol and then heated at reflux for 1-2 days. The decarboxylated product of formula (XI) is then isolated, e.g. by extraction and purified by column chromatography, if desired.

The 2-phenyl-4-($R_3$ substituted)piperidine free base, for example that of formula (XI), may then be converted to the analogous N-alkyl, N-alkenyl, N-alkynyl, N-alkylsulfonyl or N-acyl derivative of formula (I, $R_1$=H) by well known alkylation, sulfonylation or acylation techniques, as shown in Scheme B, above.

For the reagents of formula $R_2L$ preferred leaving groups, L, are the halogens, Cl, Br, or I; HO or acyloxy. For these reagents wherein $R_2$ is said alkyl, alkenyl, alkynyl, hydroxyalkyl, alkylcarbonyl, alkenylcarbonyl, alkynylcarbonyl, hydroxyalkylcarbonyl or alkylsulfonyl, an especially preferred leaving group is Cl, Br or I.

When $R_2$ is said alkylcarbonyl, alkenylcarbonyl, alkynylcarbonyl or hydroxyalkylcarbonyl, preferred leaving groups, L, are OH or acyloxy where said acyl is the residue of an acid anhydride or a mixed anhydride.

The reactions of reagents $R_2L$ with free bases such as those of formula (X) for example, are carried out by methods well known in the art for alkylation or acylation of secondary amines to form tertiary amines or amides, respectively.

For acylation of the piperidine free bases of formula (XI) the acylating agent, $R_2L$, is preferably the appropriate carboxylic acid or activated derivative thereof, for example, the acid chloride, acid bromide or acid anhydride. The reaction is preferably carried out in the presence of a reaction inert solvent, preferably, methylene chloride, chloroform, ethyl ether, tetrahydrofuran, acetone or acetonitrile and optionally in the presence of an acid acceptor which may be organic or inorganic. Suitable binding agents are, for example, the alkali metal carbonates and hydroxides, pyridine, 4-N,N-dimethylaminopyridine, triethylamine and N-methylmorpholine. The acylation is preferably carried out at a temperature of from 0° up the the reflux temperature of the solvent. When the acylation agent, $R_2L$, is a carboxylic acid it is preferred to carry out the reaction in the presence of one of the condensing agents known to be useful in forming amides, e.g., dicyclohexylcarbodiimide.

When the piperidine free base (XI) is to be alkylated with the reagent $R_2L$ an especially preferred reagent is $R_2Cl$ or $R_2Br$. The reaction is conducted in a solvent, e.g. an alkanol such as ethanol, n-butanol or isoamylalcohol at a temperature of from about room temperature up to the reflux temperature of the solvent. An acid acceptor, e.g. those set forth above and especially potassium carbonate or triethylamine, is also preferably employed in this reaction.

An alternative method for obtaining invention compounds wherein $R_2$ is alkyl or hydroxyalkyl is to carry out the above described acylation of, e.g. a compound of formula (XI), followed by reduction of the resulting amide of formula (XII) with, e.g. lithium aluminum hydride, to provide the desired compound of formula (XII) wherein $R_2$ is said alkyl, alkenyl or alkynyl. When the acylation is carried out with an hydroxyalkyl carboxylic acid, the hydroxy group of which is protected, or an activated derivative thereof, e.g. a benzyloxyalkyl carboxylic acid or an activated derivative such as the acid chloride, and the resulting amide is reduced with lithium aluminum hydride and the benzyl protecting groups subsequently removed, e.g. by hydrogenolysis, the product obtained is of formula (I) wherein $R_1$ is hydrogen and $R_2$ is hydroxyalkyl.

The requisite N-$R_2$-substituted 4-oxo-1,2,3,4-tetrahydropyridine starting materials of formula (IV) are obtained by methods described by Haider et al., *Helvetica Chimica Acta*, 58, 1287 (1975) and in references set forth therein. A preferred method is by sodium borohydride reduction of the corresponding N-$R_2$-substituted-pyridone in an alcoholic solvent, e.g. t-butanol. At 25° C. the reaction proceeds in high yield after 2 days, and the product is isolated by standard methods.

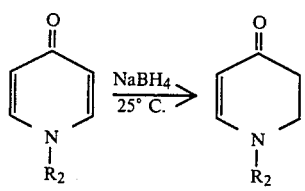

A preferred 4-oxopyridone reagent for this reaction is one where $R_2$ is alkoxycarbonyl, e.g. ethoxycarbonyl.

Esters of compounds of formula (I) wherein $R_1$ is benzoyl, alkanoyl or $-CO-(CH_2)_p-NR_4R_5$ are readily prepared by reacting forumla (I) compounds wherein $R_1$ is hydrogen with benzoic acid, the appropriate alkanoic acid or acid of formula $HOOC-(CH_2)_p-NR_4R_5$ in the presence of a condensing agent such as dicyclohexylcarbodiimide. Alternatively, they are prepared by reaction of the formula (I) ($R_1$=H) compound with the appropriate acid chloride or anhydride, e.g., benzoyl chloride, acetyl chloride or acetic anhdride, in the presence of a base such as pyridine.

The presence of a basic group in the ester moiety ($OR_1$) in the compounds of this invention permits formation of acid-addition salts involving said basic group. When the herein described basic esters are prepared via condensation of the appropriate amino acid hydrochloride (or other acid addition salt) with the appropriate compound of formula (I) in the presence of a condensing agent, the hydrochloride salt of the basic ester is produced. Careful neutralization affords the free base. The free base form can then be converted to other acid addition salts by known procedures.

Acid addition salts can, of course, as those skilled in the art will recognize, be formed with the invention compounds of formula (I) having a basic nitrogen moiety. Such salts are prepared by standard procedures. The basic ester derivatives of these piperidine compounds are, of course, able to form mono- or di-acid addition salts because of their dibasic functionality.

The analgesic properties of the compounds of this invention are determined by tests using thermal nociceptive stimuli, such as the mouse tail flick procedure, or chemical nociceptive stimuli, such as measuring the ability of a compound to suppress phenylbenzoquinone irritant-induced writhing in mice. These tests and others are described below.

TESTS USING THERMAL NOCICEPTIVE STIMULI

(a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a $\frac{1}{8}''$ thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder ($6\frac{1}{2}''$ diameter) resting on the hot plate, and timing is begun when the animal's feet touch the plate. At 0.5 and 2 hours after treatment with the test compound, the mouse is observed for the first "flicking" movements of one or both hind feet, or until 10 seconds elapse without such movements. Morphine has an $MPE_{50}=4$–5.6 mg/kg (s.c.).

(b) Mouse Tail Flick Analgesic Testing

Tail flick testing in mice is modified after D'Amour and Smith, *J. Pharmacol. Exp. Ther.*, 72, 74–79 (1941), using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg/kg (s.c.).

(c) Tail Immersion Procedure

The method is a modification of the receptacle procedure developed by Benbasset, et. al., Arch. int. *Pharmacodyn.*, 122, 434 (1959). Male albino mice (19–21 g) of the Charles River CD-1 strain are weighed and marked for identification. Five animals are normally used in each drug treatment group with each animal serving as its own control. For general screening purposes, new test agents are first administered at a dose of 56 mg/kg intraperitoneally or subcutaneously, delivered in a volume of 10 ml/kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trail is an energetic jerk or twitch of the tail coupled with a motor response. In some cases, the endpoint may be less vigorous post drug. To prevent undue tissue damage, the trail is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

TEST USING CHEMICAL NOCICEPTIVE STIMULI

Suppresion of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

TESTS USING PRESSURE NOCICEPTIVE STIMULI EFFECT ON THE HAFFNER TAIL PINCH PROCEDURE

A modification of the procedure of Haffner, *Experimentelle Prufung Schmerzstillender. Mittel Deutch Med. Wschr.*, 55, 731–732 (1929) is used to ascertain the effects of the test compound on aggressive attacking responses elicited by a stimulus pinching the tail. Male albino rats (50–60 g) of the Charles River (Sprague-Dawley) CD-strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack reported in seconds. The clamp is removed in 30 seconds if attacking has not yet occurred, and the latency of response is recorded as 30 seconds. Morphine is active 17.8 mg/kg (i.p.).

TESTS USING ELECTRICAL NOCICEPTIVE STIMULI THE "FLINCH-JUMP" TEST

A modification of the flinch-jump procedure of Tenen, *Psychopharmacologia*, 12, 278–285 (1968) is used for determining pain thresholds. Male albino rats (175–200 g) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72, and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \ MPE = \frac{\text{test time} - \text{control time}}{\text{cutoff time} - \text{control time}} \times 100$$

As mentioned above, the compounds of the invention are especially useful as antiemetic and antinausea agents in mammals. They are particularly useful in preventing emesis and nausea induced by antineoplastic agents.

The antiemetic properties of the compounds of formula (I) are determined in unanesthetized unrestrained cats according to the procedure described in Proc. Soc. Exptl. Biol. and Med., 160, 437–440 (1979).

ANTAGONISM OF $PGE_2$* DIARRHEA IN MICE

*Prostaglandin $E_2$.

The antidiarrheal activity of the invention compounds is determined by a modification of the method of Dajani et al., *European Jour. Pharmacol.*, 34, 105–113 (1975). This method reliably elicits diarrhea in otherwise untreated mice within 15 minutes. Pretreated animals in which no diarrhea occurs are considered protected by the test agent. The constipating effects of test agents are measured as an "all or none" response, diarrhea being defined as watery unformed stools, very different from normal fecal matter, which consists of well-formed boluses, firm and relatively dry.

Male albino mice of the Charles River CD-1 strain are used. They are kept in group cages and tested within one week following arrival. The weight range of the animals when tested is between 20–25 g. Pelleted rat chow is avilable ad libitum until 18 hours prior to testing, at which time food is withdrawn.

Animals are weighed and marked for identification. Five animals are normally used in each drug treatment group. Mice weighing 20–25 g are housed in group cages, and fasted overnight prior to testing. Water is available ad libitum. Animals are challenged with $PGE_2$ (0.32 mg/kg i.p. in 5% ETOH) one hour after drug treatment, and immediately placed individually in transparent acrylic boxes of $15 \times 15 \times 18$ cm. A disposable cardboard sheet on the bottom of the box is checked for diarrhea on an all or nothing basis at the end of 15 minutes. A vehicle $+PGE_2$ treatment group and a vehicle treatment group serve as controls in each day's testing.

The data are analyzed using weighted linear regression of probit-response onlog dose, employing the maximum likelihood procedure. A computer program prints results in an analysis of linear regression format, including degrees of freedom, sum of squares, mean squares and critical values of $F_{05}$ and Chi square. If the regression is significant, the $ED_{30}$, $ED_{50}$, $ED_{70}$, and $ED_{90}$ and then 95% confidence limits are calculated.

The compounds of the present invention are active analgesics, antidiarrheals, antiemetics or antinauseants via oral and parenteral administration and are conveniently administered for these uses in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, solutions, emulsions, syrups and elixirs which may contain flavoring and coloring agents. For oral administration of the therapeutic agents of this invention, tablets or capsules containing from about 0.01 to about 100 mg are suitable for most applications.

Suspensions and solutions of these drugs, particularly those wherein $R_1$ is hydrogen, are generally prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

The physician will determine the dosage which will be most suitable for an individual patient and it will vary with the age, weight and response of the particular patient and the route of administration. Generally, however, the initial analgesic dosage, as well as the initial dosage for prevention or treatment of nausea, in adults may range from 0.01 to 500 mg per day in single or divided doses. In many instances, it is not necessary to exceed 100 mg daily. The favored oral dosage range is from about 0.01 to about 300 mg/day; the preferred range is from about 0.10 to about 50 mg/day. The favored parenteral dose is from about 0.01 to about 100 mg/day; the preferred range from about 0.01 to about 20 mg/day.

The invention is further illustrated by the following Examples. Abbreviations used in the Examples are: PMR, proton magnetic resonance; s, singlet; d, doublet; dd, double doublet; t, triplet; q, quartet; m, multiplet; Ar, aromatic; b, broad; IR, infrared spectrum; HRMS, high resolution mass spectrum; M+, molecular ion.

EXAMPLE 1

N-Ethoxycarbonyl-2-[2-benzyloxy-4-(1,1-dimethylheptyl)phenyl]-4-piperidinone

To 3.45 (0.142 mole) of magnesium is added a solution of 27.6 g (0.071 mole) of 2-benzyloxy-1-bromo-4-(1,1-dimethylheptyl)benzene in 71 ml of tetrahydrofuran, at such a rate that gentle reflux occurs. The Grignard solution is allowed to cool to 25° C. over 30 minutes, diluted with 71 ml of ether, the mixture cooled to −12° C. and 2.13 g (0.0112 mole) cuprous iodide is added followed by addition of 8.00 g (0.0473 mole) of N-ethoxycarbonyl-2,3-dihydro-4(1H)-pyridinone in 47 ml of ether over 20 minutes. The reaction is stirred 30 minutes longer at −12° C. and then added to 2 liters ether and 600 ml saturated ammonium chloride. The organic extract is washed with three 600 ml portions of saturated ammonium chloride, dried over magnesium sulfate and evaporated to an oil. This crude product is purified via column chromatography on 2 kg of silica gel eluting in 500 ml fractions with 50% ether-hexane to yield (fractions 17-24) 16.0 g (71%) of the title compound as an oil.

PMR (CDCl$_3$) ppm (delta): 1.22 (s, gem CH$_3$), 2.47 (dd, J=7 and 5 Hz, CH$_2$), 2.91 (d, J=5 Hz, CH$_2$), 3.3-4.4 (m, CH$_2$), 4.09 (q, J=7 Hz, CH$_2$), 5.10 (s, OCH$_2$), 5.77 (t, J=6 Hz, CH), 6.8 (m, Ar, 2H), 7.10 (d, J=8 Hz, Ar, 1H), 7.39 (m, Ar, 5H).

IR (CHCl$_3$) 1721, 1681, 1605, 1570 cm$^{-1}$.

HRMS (m/e) 479.3278 (M+, Calcd. for C$_{30}$H$_{41}$NO$_4$: 479.3025), 406, 388, 91.

EXAMPLE 2

N-Ethoxycarbonyl-cis-2-[2-benzyloxy-4-(1,1-dimethylheptyl)phenyl]-4-piperidinol

To a −50° C. solution of 12.1 g (25.1 mmol) of N-ethoxycarbonyl-2-[2-benzyloxy-4-(1,1-dimethylheptyl)-phenyl]-4-piperidinone in 90 ml methanol and 90 ml of tetrahydrofuran is added 1.04 g (27.5 mmole) of sodium borohydride. The reaction is stirred 2 hours at −50° C. and then allowed to warm to 25° C. The reaction is quenched by addition to 300 ml saturated sodium chloride and the mixture extracted with ethyl ether (2 liters). The organic extract is washed with 300 ml saturated sodium chloride, dried over magnesium sulfate and the ether evaporated in vacuo. The crude product is purified via column chromatography on 2 kg silica gel eluting in 500 ml fractions with 2% methanol-5% ether-93% dichloromethane to yield (fractions 20-26) 6.04 g (50%) of the title compound as an oil and 3.75 g (31%) of a mixture of the title compound and its trans-isomer. Further chromatography yields pure trans-isomer.

Cis-Isomer

PMR (CDCl$_3$), ppm (delta): 1.22 (s, gem CH$_3$), 3.2-4.2 (m, CH$_2$, CH), 4.02 (q, J=7 Hz, CH$_2$), 5.07 (s, OCH$_2$), 5.35 (t, J=6 Hz, CH), 6.8 (m, Ar, 2H), 7.06 (d, J=8 Hz, Ar, 1H), 7.35 (m, Ar, 5H).

IR (CHCl$_3$) 3559, 3443, 1672, 1610, 1572 cm$^{-1}$.

HRMS (m/e) 481.3154 (M+, Calcd. for C$_{30}$H$_{43}$NO$_4$: 481.3181), 408, 390, 91. Trans-Isomer PMR (CDCl$_3$) ppm (delta): 1.22 (s, gem CH$_3$), 2.55 (m), 3.0-4.3 (m), 4.02 (q, J=7 Hz, CH$_2$), 5.08 (s, OCH$_2$), 5.68 (bd, J=6 Hz, 1H), 6.8 (m, Ar, 3H), 7.35 (m, Ar, 5H).

HRMS (m/e) 481.3275 (M+, Calcd. for C$_{30}$H$_{43}$NO$_4$: 481.3181), 463, 408, 390, 91.

EXAMPLE 3

Cis-2-[2-benzyloxy-4-(1,1-dimethylheptyl)phenyl]-4-piperidinol

To a solution of 4.62 g (9.59 mmole) of N-ethoxycarbonyl-cis-2-[2-benzyloxy-4-(1,1-dimethylheptyl)-phenyl]-4-piperidinol in 5 ml ethanol is added a solution of 4.2 g (75 mmole) of potassium hydroxide in 25 ml ethylene glycol and 4.2 ml water. The resultant mixture is evaporated at reduced pressure to remove ethanol and is then heated to reflux (bath 185° C.). After 24 hours material boiling at 80°-100° C. is removed by distillation, 6 ml ethylene glycol is added and the reaction continued at reflux for 17 hours. After cooling, the mixture is added to 500 ml dichloromethane and 80 ml water. The organic extract is washed with 80 ml saturated sodium chloride, dried over magnesium sulfate and evaporated in vacuo. The resulting crude oil is purified via column chromatography on 300 g of silica gel eluting in 20 ml fractions with 2.5% triethylamine, 2.5% methanol, 95% ethyl ether (fractions 1-109) and 5% triethylamine, 5% methanol, 90% ethyl ether (fractions 110-200). Fractions 138-190 gave 3.13 g (83%) of the title compound.

PMR (CDCl$_3$) ppm (delta): 1.22 (s, gem CH$_3$), 3.8 (m, 1H), 4.0 (m, 1H), 5.05 (s, OCH$_2$), 6.9 (m, Ar, 2H), 7.35 (m, Ar, 6H).

IR (CHCl$_3$) 3546, 3279, 1608, 1621 cm$^{-1}$.

HRMS (m/e) 409.2886 (M+, Calcd. for C$_{27}$H$_{39}$NO$_2$: 409.2971), 392, 364, 318, 135, 91.

EXAMPLE 4

N-Ethoxycarbonyl-2-[4-(1,1-dimethylheptyl)-2-hydroxyphenyl]-4-piperidinone

A mixture of 369 mg (0.77 mmole) of N-ethoxycarbonyl-2-[2-benzyloxy-4-(1,1-dimethylheptyl)phenyl]-4-piperidinone and 414 mg of 5% palladium on carbon (50% wet) in 5 ml ethanol was stirred under 1 atmosphere of hydrogen at 25° C. until the hydrogen uptake is complete (approximately 3 hours). The reaction is filtered through a filter aid, washing with ethanol and the filtrate evaporated in vacuo. The residual crude oil is purified via column chromatography on 22 g of silica gel eluting in 4 ml fractions with 15% ethyl ether in dichloromethane to yield (fractions 28–42) 174 mg (57%) of the title compound as an oil.

PMR (CDCl$_3$) ppm (delta): 0.83 (m, CH$_3$), 1.25 (s, gem —CH$_3$), 3.7–4.4 (m), 5.45 (m, 1H), 6.7–7.2 (m, Ar, 3H).

IR (CHCl$_3$) 3559, 3333, 1678, 1623, 1575 cm$^{-1}$.

HRMS (m/e) 389.2544 (M+, Calcd. for C$_{23}$H$_{35}$NO$_4$: 389.2557), 316, 304, 300, 273, 258, 161, 142.

EXAMPLE 5

N-Methyl-cis-2-[2-benzyloxy-4-(1,1-dimethylheptyl)phenyl]-4-piperidinol

To a 25° C. slurry of 267 mg (7.04 mmole) of lithium aluminum hydride in 12 ml ethyl ether is added dropwise over 30 minutes a solution of 1.50 g (3.11 mmole) of N-ethoxycarbonyl-cis-2-[2-benzyloxy-4-(1,1-dimethylheptyl)phenyl]-4-piperidinol. The reaction is stirred for 0.5 hour at 25° C., then two hours at reflux. The reaction is quenched by addition of wet magnesium sulfate followed by decantation and washing of the salts with two 30 ml portions of ether. The ether extract is washed with 10 ml saturated sodium chloride, dried over magnesium sulfate and evaporated to give 1.19 g (91%) of the title compound as a solid.

PMR (CDCl$_3$) ppm (delta): 0.82 (m, CH$_3$), 1.24 (s, gem —CH$_3$), 2.00 (s, N—CH$_3$), 3.0 (m, 1H), 3.4–4.0 (m, 2H), 5.04 (s, OCH$_2$), 6.9 (m, Ar, 2H), 7.35 (m, Ar, 6H).

IR (CHCl$_3$) 3571, 3378, 1613, 1575 cm$^{-1}$.

HRMS (m/e) 423.3100 (M+, Cacld. for C$_{28}$H$_{41}$NO$_2$: 423.3127), 408, 332, 314, 300, 246, 91.

EXAMPLE 6

N-Methyl-cis-2-[4-(1,1-dimethylheptyl)-2-hydroxyphenyl]-4-piperidinol

Using the procedure of Example 4, 1.13 g (2.68 mmole) of N-methyl-cis-2-[2-benzyloxy-4-(1,1-dimethylheptyl)phenyl]-4-piperidinol and 452 mg of 5% palladium on carbon (50% wet) affords 0.752 g (84%) of the title compound as an oil.

PMR (CDCl$_3$) ppm (delta): 0.80 (m, CH$_3$), 1.22 (s, gem CH$_3$), 2.16 (s, NCH$_3$), 2.9–4.0 (m), 6.7 (m, Ar, 3H).

IR (CHCl$_3$) 3571, 3425, 1623, 1572, 1502 cm$^{-1}$.

HRMS (m/e) 333.2650 (M+, Calcd. for C$_{21}$H$_{35}$NO$_2$: 333.2659), 318, 316, 249, 114.

EXAMPLE 7

A.
N-Ethoxycarbonyl-cis-2-[4-(1,1-dimethylheptyl)-2-hydroxyphenyl]-4-piperidinol Using the procedure of Example 4, 423 mg (0.878 mmole) of N-ethoxycarbonyl-cis-2-[2-benzyloxy-4-(1,1-dimethylheptyl)phenyl]-4-piperidinol and 210 mg of 5% palladium on carbon (50% wet) provides 265 mg (77%) of the title compound as an oil.

PMR (CDCl$_3$) ppm (delta): 0.82 (m, CH$_3$), 1.22 (s, gem CH$_3$), 3.0–4.2 (m), 4.04 (q, J=7 Hz, CH$_2$), 5.26 (t, J=6 Hz, CH), 6.75 (m, Ar, 2H), 7.51 (d, J=8 Hz, Ar, H).

IR (CHCl$_3$) 3684, 3589, 3216, 1649, 1564 cm$^{-1}$.

HRMS (m/e) 391.2699 (M+, Calcd. for C$_{23}$H$_{37}$NO$_4$: 391.2713), 318, 306, 300, 161.

B.
Cis-2-[4-(1,1-dimethylheptyl)-2-hydroxyphenyl]-4-piperidinol

Similarly, 758 mg (1.85 mmol) of cis-2-[2-benzyloxy-4-(1,1-dimethylheptyl)phenyl]-4-piperidinol and 303 mg of 5% palladium-on-carbon (50% wet) yields 403 mg (68%) of the title compound, M.P. 97°–102° (dichloromethane-pentane).

PMR (CDCl$_3$) ppm (delta): 0.80 (m, CH$_3$), 1.22 (s, gem —CH$_3$), 1.22–4.8 (m), 6.8 (m, Ar, 3H).

IR (CHCl$_3$) 3559, 3378, 3279, 1623, 1570, 1493 cm$^{-1}$.

HRMS (m/e) 319.2465 (M+, Calcd. for C$_{20}$H$_{33}$NO$_2$: 319.2503), 302, 274, 163, 161, 148, 100.

EXAMPLE 8

N-Propionyl-cis-2-[2-benzyloxy-4-(1,1-dimethylheptyl)phenyl]-4-propionylpiperidine To a 25° C. solution of 689 mg (1.68 mmole) cis-2-[2-benzyloxy-4-(1,1-dimethylheptyl)phenyl]-4-piperidinol and 1.02 g (8.36 mmole) 4-N,N-dimethylaminopyridine in 2.6 ml dichloromethane is added, at once, 0.64 ml (5.0 mmole) of propionic anhydride. The reaction is stirred 3 hours and then added to a mixture of 20 ml 1N hydrochloric acid and 100 ml ethyl ether. The organic layer is washed with 15 ml 1N hydrochloric acid, 25 ml saturated sodium bicarbonate, 20 ml saturated sodium chloride, dried over magnesium sulfate and the solvent is evaporated to afford an oil. The crude product is purified via column chromatography on 50 g of silica gel eluting in 10 ml fractions with 20% hexane in ethyl ether to give 768 mg (88%) of the title compound as an oil.

PMR (CDCl$_3$) ppm (delta): 0.62–1.3 (m, all CH$_3$), 4.5 (m, 1H), 5.05 (s, OCH$_2$), 5.37 (m, 1H), 6.8 (m, Ar, 2H), 7.00 (d, J=8 Hz, Ar, H), 7.35 (q, Ar, 5H).

IR (CHCl$_3$) 1736, 1639, 1575 cm$^{-1}$.

EXAMPLE 9

N-Propyl-cis-2-[4-(1,1-dimethylheptyl)-2-hydroxyphenyl]-4-piperidinol

A.
N-Propyl-cis-2-[2-benzyloxy-4-(1,1-dimethylheptyl)phenyl]-4-piperidinol Using the procedure of Example 5, 723 mg (1.46 mmole) of N-propionyl-cis-2-[2-benzyloxy-4-(1,1-dimethylheptyl)phenyl]-4-propionyloxypiperidine and 129 mg (3.40 mmole) of lithium aluminum hydride gives 582 mg (88%) of the title compound as an oil.

PMR (CDCl$_3$) ppm (delta): 0.6–1.22 (m, all CH$_3$), 2.9–4.0 (m, 4H), 5.04 (s, OCH$_2$), 6.85 (m, Ar, 2H), 7.35 (m, Ar, 6H).

IR (CHCl$_3$) 3571, 3390, 1613, 1575 cm$^{-1}$.

HRMS (m/e) 451.3449 (M+, Calcd. for C$_{30}$H$_{45}$NO$_2$: 451.3439), 422, 404, 91.

B. Employing the procedure of Example 4, 535 mg (1.18 mmole) N-propyl-cis-2-[2-benzyloxy-4-(1,1-dimethylheptyl)phenyl]-4-piperidinol and 212 mg 5% palladium on carbon (50% wet) gives 402 mg (94%) of the title compound as an oil.

PMR (CDCl$_3$) ppm (delta): 0.65–1.25 (m, all CH$_3$), 3.0–4.0 (m, 3H), 6.75 (s, Ar, 3H).

IR (CHCl$_3$) 3521, 3367, 1613, 1565 cm$^{-1}$.

HRMS (m/e) 361.2963 (M+, Calcd. for C$_{23}$H$_{39}$NO$_2$: 361.2971), 332, 314, 271.

EXAMPLE 10

N-(2-Propenyl)-cis-2-[2-benzyloxy-4-(1,1-dimethylheptyl)phenyl]-4-piperidinol

A mixture of 778 mg (1.90 mmole) of cis-2-[2-benzyloxy-4-(1,1-dimethylheptyl)phenyl]-4-piperidinol, 160 microliters (1.84 mmole) of 1-bromo-2-propene and 300 mg (2.17 mmole) of potassium carbonate in 10 ml ethanol is stirred at 25° C. for 20.5 hours. An additional 4 microliters of 1-bromo-2-propene is added to the reaction and stirring continued for 7 hours. The reaction mixture is then added to 50 ml saturated sodium chloride and extracted with 250 ml ethyl ether. The ether extract is dried over magnesium sulfate and the solvent is evaporated. The resulting oil is purified via column chromatography on 28 g of silica gel eluted in 7 ml fractions with 1:3 methanol/ethyl ether to yield (fractions 10–35) 518 mg (61%) of the title compound as an oil.

PMR (CDCl$_3$) ppm (delta): (m, CH$_3$), 1.22 (s, gem —CH$_3$), 3.0–4.0 (m, 5H), 4.8–5.2 (m, vinyl 2H), 5.02 (s, OCH$_2$), 5.3–6.2 (m, vinyl H), 6.9 (m, Ar, 2H), 7.35 (m, Ar, 6H).

IR (CHCl$_3$) 3584, 3436, 1675, 1647, 1618, 1580 cm$^{-1}$.

HRMS (m/e) 449.3199 (M+, Calcd. for C$_{30}$H$_{43}$NO$_2$: 449.3283), 432, 408, 390, 358, 340, 328, 140, 91.

EXAMPLE 11

N-(2-Propenyl)-cis-2-[4-(1,1-dimethylheptyl)-2-hydroxyphenyl]-4-piperidinol

A solution of 6.8 ml (74.6 mmole) of propanethiol in 75 ml of tetrahydrofuran is degassed by three freeze-thaw cycles at 0.1 torr. The resultant solution is cooled to −78° C. and 28 ml of 2.5M n-butyllithium in hexane is added. The reaction is then allowed to warm to 25° C. and stirred 3 hours longer. The reaction is evaporated to dryness under high vacuum and the residue dissolved in 70 ml of degassed hexamethylphosphoramide. To a 25° C. degassed solution of 218 mg (0.486 mmole) of N-(2-propenyl)-cis-2-[2-benzyloxy-4-(1,1-dimethylheptyl)phenyl]-4-piperidinol in 1 ml of hexamethylphosphoramide is added 2.2 ml of the above prepared solution of lithium propanethiolate. The reaction is stirred 30 minutes at 25° C. and 1.5 hour at 105° C. followed by cooling to 25° C. The reaction is quenched by addition to 30 ml water and the mixture extracted with 150 ml ethyl ether. The ether extract is washed twice with 30 ml water, once with 30 ml saturated sodium chloride, dried over magnesium sulfate and evaporated to an oil. The crude product is purified via column chromatography on 48 g of silica gel eluting in 8 ml fractions with ethyl ether to give (fractions 12–24) 101 mg (58%) of the title compound as an oil.

PMR (CDCl$_3$) ppm (delta): 0.80 (m, CH$_3$), 1.24 (s, gem —CH$_3$), 2.9–4.2 (m, 5H), 5.15 (m, vinyl 2H), 5.4–6.3 (m, vinyl H), 6.85 (m, Ar, 3H).

IR (CHCl$_3$) 3546, 3390, 1618, 1572, 1495 cm$^{-1}$.

HRMS (m/e) 359.2830 (M+, Calcd. for C$_{23}$H$_{37}$NO$_2$: 359.2815), 318, 300, 275, 140.

EXAMPLE 12

N-Methoxycarbonyl-cis-2-[4-(1,1-dimethylheptyl)-2-hydroxyphenyl]-4-piperidinol

A. N-Methoxycarbonyl-cis-2-[2-benzyloxy-4-(1,1-dimethylheptyl)phenyl]-4-piperidinol To a 0° C. solution of 193 mg (0.471 mmole) of cis-2-[2-benzyloxy-4-(1,1-dimethylheptyl)phenyl]-4-piperidinol and 0.29 ml triethylamine in 2.2 ml tetrahydrofuran is added dropwise 40 microliters (0.518 mmole) of methyl chloroformate. The reaction is stirred 40 minutes and then another 10 microliters of methyl chloroformate is added. The reaction is stirred 40 minutes longer, diluted with ether and filtered. The filtrate is washed with saturated sodium bicarbonate and saturated sodium chloride, dried over magnesium sulfate and evaporated to an oil. The crude product is purified via column chromatography on 10.4 g of silica gel eluting in 3 ml fractions with 1:3 ethyl ether/hexane to yield (fractions 16–30) 198 mg (80%) of the title compound as an oil.

PMR (CDCl$_3$) ppm (delta): 0.82 (m, CH$_3$), 1.20 (s, gem CH$_3$), 3.57 (s, OCH$_3$), 4.1 (m, CH), 5.02 (s, OCH$_2$), 5.33 (bt, J=6 Hz, CH), 6.85 (m, Ar, 2H), 7.00 (d, J=8 Hz, Ar, H), 7.27 (s, Ar, 5H).

IR (CHCl$_3$) 3521, 3390, 1681, 1597, 1570, 1490 cm$^{-1}$.

HRMS (m/e) 467.3070 (M+, Calcd. for C$_{29}$H$_{41}$NO$_4$: 467.3025), 449, 409, 408, 376, 158, 91.

B. Debenzylation of 177 mg (0.377 mmole) of N-methoxycarbonyl cis-2-[2-benzyloxy-4-(1,1-dimethylheptyl)phenyl]-4-piperidinol with 144 mg of 5% palladium on carbon (50% wet) by the procedure of Example 4 affords 81.3 mg (57%) of the title compound as an oil, 4.1 mg (3%) of by-product 5-(1,1-dimethylheptyl)-2-[3-hydroxy-5-(N-methoxycarbonylamino)pentyl]phenol as an oil, and 49.2 mg (35%) of a mixture of the two.

Title Compound

PMR (CDCl$_3$) ppm (delta): 0.8 (m, CH$_3$), 1.22 (s, gem —CH$_3$), 3.66 (s, OCH$_3$), 4.15 (m, CH), 5.36 (bt, J=7 Hz, CH), 6.8 (m, Ar, 2H), 7.55 (d, J=8 Hz, Ar, H).

IR (CHCl$_3$) 3534, 3145, 1647, 1616, 1560 cm$^{-1}$.

HRMS (m/e) 377.2565 (M+, Calcd. for C$_{22}$H$_{35}$NO$_4$: 377.2557), 318, 292, 260, 161.

By-Product

HRMS (m/e) 379.2699 (M+, Calcd. for C$_{22}$H$_{37}$O$_4$: 379.2713), 361, 347, 318, 147.

EXAMPLE 13

N-Methylsulfonyl-cis-2-[4-(1,1-dimethylheptyl)-2-hydroxyphenyl]-4-piperidinol

A. N-Methylsulfonyl-cis-2-[2-benzyloxy-4-(1,1-dimethylheptyl)phenyl]-4-piperidinol Reacting 409 mg (0.997 mmol) of cis-2-[2-benzyloxy-4-(1,1-dimethylheptyl)phenyl]-4-piperidinol and 81 microliters (1.05 mmole) of methanesulfonyl chloride by the procedure of Example 12, Part A, gives 130 mg (27%) of the mesylate as an oil.

PMR (CDCl$_3$) ppm (delta): 0.82 (m, CH$_3$), 1.22 (s, gem —CH$_3$), 2.51 (s, SCH$_3$), 5.07 (s, OCH$_2$), 6.9 (m, Ar, 2H), 7.31 (m, Ar, 6H).

IR (CHCl$_3$) 3509, 3378, 1751, 1605, 1567, 1488.

HRMS (m/e) 487.2696 (M+, Calcd. for $C_{28}H_{41}NO_4S$: 487.2746), 408, 402, 390, 91.

B. Hydrogenolysis of 121 mg (0.248 mmol) of N-methylsulfonyl-cis-2-[2-benzyloxy-4-(1,1-dimethylheptyl)phenyl]-4-piperidinol with 110 mg of 5% palladium on carbon (50% wet) by the procedure of Example 4 gives 85.3 mg (86%) of the title compound as an oil.

PMR (CDCl$_3$) ppm (delta): 0.8 (m, CH$_3$), 1.22 (s, gem —CH$_3$), 2.46 (s, SCH$_3$), 4.67 (t, J=7 Hz, CH), 6.85 (m, Ar, 2H), 7.22 (d, J=8 Hz, Ar, H).

IR (CHCl$_3$) 3534, 3344, 1613, 1563, 1493 cm$^{-1}$.

HRMS (m/e) 397.2253 (M+, Calcd. for $C_{21}H_{35}NO_4S$: 397.2313), 318, 312, 300, 294, 161.

EXAMPLE 14

N-(3-Hydroxypropionyl)-cis-2-[4-(1,1-dimethylheptyl)-2-hydroxyphenyl]-4-piperidinol

A.

N-(3-Benzyloxy)propionyl-cis-2-[2-benzyloxy-4-(1,1-dimethylheptyl)phenyl]-4-piperidinol To a solution of 789 mg (1.93 mmole) of cis-2-[2-benzyloxy-4-(1,1-dimethylheptyl)phenyl]-4-piperidinol and 347 mg (1.93 mmole) of 3-benzyloxypropionic acid in 2.5 ml of dichloromethane is added 403 mg (1.95 mmole) of dicyclohexylcarbodiimide. The reaction is stirred for 3.5 hours and then an additional 42.9 mg of dicyclohexylcarbodiimide is added. The reaction is stirred 18 hours longer and then filtered. The filtrate is washed with 1N hydrochloric acid, saturated sodium bicarbonate solution, dried over magnesium sulfate and evaporated to an oil. This crude product is purified via column chromatography on 78 g of silica gel, eluting in 16 ml fractions with 1:3 ethyl ether/hexane to give 712 mg (65%) of the desired amide as an oil which is used in the next step.

PMR (CDCl$_3$) ppm (delta): 0.82 (m, CH$_3$), 1.20 (s, gem CH$_3$), 4.47 (s, OCH$_2$), 5.08 (s, OCH$_2$), 5.4 (m, 1H), 6.95 (m, Ar, H), 7.23 (s, Ar, 5H), 7.36 (s, Ar, 5H).

IR (CHCl$_3$) 3623, 3460, 1626, 1572, 1481 cm$^{-1}$.

HRMS (m/e) 571.3584 (M+, Calcd. for $C_{37}H_{49}NO_4$: 571.3649), 480, 408, 318, 91.

B. Hydrogenolysis of 710 mg (1.24 mmole) of N-(3-benzyloxypropionyl)-cis-2-[2-benzyloxy-4-(1,1-dimethylheptyl)phenyl]-4-piperidinol with 700 mg of 5% palladium on carbon (50% wet) by the method of Example 4 yields 429 mg (88%) of the title compound.

M.P. 119°–121° C.

PMR (CDCl$_3$) ppm (delta): 0.82 (m, CH$_3$), 1.22 (s, gem CH$_3$), 3.3–4.3 (m), 5.59 (t, J=7 Hz, CH), 6.8 (m, Ar, 2H), 7.57 (d, J=8 Hz, Ar, H).

IR (CHCl$_3$) 3571, 3125, 1587 cm$^{-1}$.

HRMS (m/e) 391.2716 (M+, Calcd. for $C_{23}H_{37}NO_4$: 391.2713), 374, 319, 318, 302, 161.

Analysis: Calcd. for $C_{23}H_{37}NO_4$: C, 70.55; H, 9.53; N, 3.58. Found: C, 70.66; H, 9.19; N, 3.61.

EXAMPLE 15

N-Butyryl-cis-2-[4-(1,1-dimethylheptyl)-2-hydroxyphenyl]-4-piperidinol

A.

N-Butyryl-cis-2-[2-benzyloxy-4-(1,1-dimethylheptyl)phenyl]-4-piperidinol

Acylation of 421 mg (1.03 mmole) of cis-2-[2-benzyloxy-4-(1,1-dimethylheptyl)phenyl]-4-piperidinol with 110 mg (1.03 mmol) of butyryl chloride by the procedure of Example 12, Part A, gives 530 mg (96%) of the desired amide as an oil.

PMR (CDCl$_3$) ppm (delta): 0.8–1.2 (m, all CH$_3$), 5.10 (s, OCH$_2$), 5.35 (m, CH), 6.85 (m, Ar, 2H), 7.04 (d, J=8 Hz, Ar, H), 7.35 (s, Ar, 5H).

IR (CHCl$_3$) 3655, 3587, 3451, 1627, 1572 cm$^{-1}$.

HRMS (m/e) 479.3418 (M+, Calcd. for $C_{31}H_{45}NO_3$: 479.3388), 408, 388, 372, 318, 300, 100, 91.

B. Debenzylation of 529 mg (1.10 mmol) of the product of Part A, above with 301 mg of 5% palladium on carbon (50% wet) by the method of Example 4 affords 334 mg (78%) of the title compound as an oil.

PMR (CDCl$_3$) ppm (delta): 0.7–1.2 (m, all CH$_3$), 3.55 (m, CH$_2$), 4.05 (m, CH), 5.61 (t, J=7 Hz, CH), 6.8 (m, Ar, 2H), 7.62 (d, J=8 Hz, Ar, H).

IR (CHCl$_3$) 3686, 3591, 3448, 1548, 1499 cm$^{-1}$.

HRMS (m/e) 389.2903 (M+, Calcd. for $C_{24}H_{39}NO_3$: 389.2920), 372, 318, 302, 284, 274, 257, 234, 217, 161, 100.

Employing the appropriate acid chloride in place of butyryl chloride in the procedure of Part A, above and debenzylation by the method of Part B similarly provides the following amides:

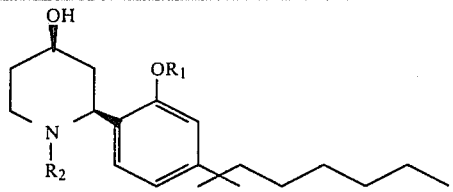

| R$_1$ | R$_2$ | Yield, % | Physical Data |
|---|---|---|---|
| benzyl | acetyl | 99 | PMR (CDCl$_3$) ppm (delta): 0.8 (m, CH$_3$), 1.22 (s, gem —CH$_3$), 1.91 (s, CH$_3$), 5.08 (s, OCH$_2$), 5.27 (m, CH), 6.82 (m, Ar, 2H), 7.03 (d, J = 8 Hz, Ar, H), 7.35 (s, Ar, 5H). IR (CHCl$_3$) 3587, 3420, 1630, 1573, 1495 cm$^{-1}$. HRMS (m/e) 451.3089 (M+, Calcd. for $C_{29}H_{41}NO_3$: 451.3076), 408, 360, 344, 318, 300, 91. |
| H | acetyl | 91 | PMR (CDCl$_3$) ppm (delta): 0.8 (m, CH$_3$), 1.22 (s, gem —CH$_3$), 2.08 (s, CH$_3$), 3.55 (m, 2H), 4.08 (m, CH), 5.57 (t, J = 7 Hz, CH), 6.81 (m, Ar, 2H), 7.63 (d, J = 8 Hz, Ar, H). IR (CHCl$_3$) 3598, 3405, 1603, 1499 cm$^{-1}$. HRMS (m/e) 361.2596 (M+ Calcd. for $C_{22}H_{35}NO_3$: 361.2608), 344, 318, 302, 234, 217, 199, 162, 161. |
| benzyl | propionyl | 100 | PMR (CDCl$_3$) ppm (delta): 1.20 (s, gem —CH$_3$), 5.06 (s, OCH$_2$), 5.29 (m, CH), 6.78 (m, Ar, 2H), 6.98 (d, J = 8 Hz, Ar, H), 7.30 (m, Ar, 5H). IR (CHCl$_3$) 3591, 3444, 1630, 1572, 1496 cm$^{-1}$. HRMS (m/e) 465.2646 (M+, Calcd. for $C_{30}H_{43}NO_3$: 465.3232), 408, 318, 91. |
| H | propionyl | 91 | PMR (CDCl$_3$) ppm (delta): 1.22 (s, gem —CH$_3$), 3.53 (m, 2H), 4.1 (m, CH), 5.63 (bt, J = 7 Hz, CH), 6.82 (m, Ar, 2H), 7.63 (d, J = 8 Hz, Ar, H). |

-continued

| $R_1$ | $R_2$ | Yield, % | Physical Data |
|---|---|---|---|
| benzyl | n-pentanoyl | 99 | IR (CHCl$_3$) 3595, 3400, 1601, 1499 cm$^{-1}$. HRMS (m/e) 375.2711 (M+, Calcd. for C$_{23}$H$_{37}$NO$_3$: 375.2764), 358, 346, 318, 302, 300, 284, 234, 217, 199. PMR (CDCl$_3$) ppm (delta): 0.8–1.2 (m, all CH$_3$), 5.10 (s, OCH$_2$), 5.30 (bt, J = 6 Hz, CH), 6.87 (m, Ar, 2H), 7.02 (d, J = 8 Hz, Ar, H), 7.36 (m, Ar, 5H). |
| H | n-pentanoyl | 47 | IR (CHCl$_3$) 3593, 3457, 1629, 1573, 1495 cm$^{-1}$. HRMS (m/e) 493.3224 (M+, Calcd. for C$_{32}$H$_{47}$NO$_3$: 493.3544), 408, 402, 386, 318, 91. PMR (CDCl$_3$) ppm (delta): 1.22 (s, gem —CH$_3$), 3.55 (m, 2H), 4.15 (m, CH), 5.60 (bt, J = 6 Hz, CH), 6.79 (m, Ar, 2H), 7.60 (d, J = 8 Hz, Ar, H). IR (CHCl$_3$) 3595, 3420, 1598, 1499 cm$^{-1}$. HRMS (m/e) 403.3072 (M+, Calcd. for C$_{25}$H$_{41}$NO$_3$: 403.3076), 387, 324. |

EXAMPLE 16

N-(3-Hydroxypropyl)-cis-2-[4-(1,1-dimethylheptyl)-2-hydroxyphenyl]-4-piperidinol Reduction of 593 mg (1.51 mmole) of N-(3-hydroxypropionyl)-cis-2-[4-(1,1-dimethylheptyl)-2-hydroxyphenyl]-4-piperidinol with 152 mg (4.01 mmole) of lithium aluminum hydride by the procedure of Example 5 provides 398 mg (70%) of the title compound as an oil.

PMR (CDCl$_3$) ppm (delta): 1.24 (s, gem —CH$_3$), 3.0–4.6 (m), 6.75 (s, Ar, 3H).

IR (CHCl$_3$) 3592, 3462, 1622, 1605, 1573 cm$^{-1}$.

HRMS (m/e) 377.2933 (M+, Calcd. for C$_{23}$H$_{39}$NO$_3$: 377.2920), 332, 314, 271, 161, 158, 88.

EXAMPLE 17

N-Formyl-cis-2-[4-(1,1-dimethylheptyl)-2-hydroxyphenyl]-4-piperidinol

A.

N-Formyl-cis-2-[2-benzyloxy-4-(1,1-dimethylheptyl)phenyl]-4-piperidinol

Using the procedure of Example 14, Part A, 1.81 g (4.42 mmole) of cis-2-[2-benzyloxy-4-(1,1-dimethylheptyl)phenyl]-4-piperidinol, 206 mg (4.48 mmole) of formic acid and 1.04 g (5.04 mmole) of dicyclohexylcarbodiimide gives 1.32 g (70%) of the corresponding formamide.

M.P. 119.5°–122.5° C. (recrystallized from methanol).

PMR (CDCl$_3$) ppm (delta): 0.82 (m, CH$_3$), 1.23 (s, gem —CH$_3$), 5.02 (s, OCH$_2$), 6.88 (m, Ar, 2H), 7.25 (m, Ar, 6H), 7.58 (s, CHO).

IR (CHCl$_3$) 3687, 3586, 3426, 1648, 1611, 1571, 1494 cm$^{-1}$.

HRMS (m/e) 437.2935 (M+, Calcd. for C$_{28}$H$_{39}$NO$_3$: 437.2920), 408, 347, 91.

B. Debenzylation of 1.31 g (2.99 mmol) of the product of Part A with 830 mg of 5% palladium on carbon (50% wet) gives 752 mg (72%) of the title compound.

M.P. 149°–150° C. (recrystallized from methanol-water).

PMR (CDCl$_3$) ppm (delta): 0.80 (m, CH$_3$), 1.25 (s, gem —CH$_3$), 6.75 (m, Ar, 2H), 7.10 (d, J=8 Hz, Ar, H), 7.49 (s, CHO).

IR (CHCl$_3$) 3593, 3250, 1644, 1585 cm$^{-1}$.

HRMS (m/e) 347.2415 (M+, Calcd. for C$_{21}$H$_{33}$NO$_3$: 347.2452), 346, 330, 262, 161.

Analysis: Calcd. for C$_{21}$H$_{33}$NO$_3$: C, 72.60; H, 9.57; N, 4.03. Found: C, 73.38; H, 9.24; N, 3.95.

EXAMPLE 18

N-Propioloyl-cis-2-[4-(1,1-dimethylheptyl)-2-hydroxyphenyl]-4-piperidinol

Repeating the procedure of Example 10, but with 760 mg (2.38 mmole) of cis-2-[4-(1,1-dimethylheptyl)-2-hydroxyphenyl]-4-piperidinol, 970 mg (11 mmole) of propynoyl chloride and 2.07 g (15 mmole) of potassium carbonate in 70 ml of tetrahydrofuran yields 430 mg (38%) of the title compound as an oil.

PMR (CDCl$_3$) ppm (delta): 0.82 (m, CH$_3$), 1.22 (s, gem —CH$_3$), 3.11 (s, CH), 5.65 (bt, J=6 Hz, CH), 6.80 (m, Ar, 2H), 7.60 (d, J=8 Hz, Ar, H).

IR (CHCl$_3$) 3595, 3296, 3200, 2110, 1621, 1602, 1500 cm$^{-1}$.

HRMS (m/e) 371.2495 (M+, Calcd. for C$_{23}$H$_{33}$NO$_3$: 371.2452), 354, 287, 286, 233, 199, 187, 161.

EXAMPLE 19

N-(2-Propynyl)-cis-2-[4-(1,1-dimethylheptyl)-2-hydroxyphenyl]-4-piperidinol

Employing the procedure of Example 10 with 321 mg (1.01 mmole) of cis-2-[4-(1,1-dimethylheptyl)-2-hydroxyphenyl]-4-piperidinol, 82 microliter (1.06 mmole) or propynyl bromide and 292 mg (2.12 mmole) of potassium carbonate affords 205 mg (57%) of the title compound as an oil.

PMR (CDCl$_3$) ppm (delta): 0.82 (m, CH$_3$), 1.25 (s, gem —CH$_3$), B 2.22 (t, J=2 Hz, ≡CH), 3.35 (d, J=2 Hz, 2H), 6.78 (Ar, 3H).

IR (CHCl$_3$) 3595, 3303, 1627, 1576, 1502 cm$^{-1}$.

HRMS (m/e) 357.2682 (M+, Calcd. for C$_{23}$H$_{35}$NO$_2$: 357.2659), 340, 318, 233, 138.

EXAMPLE 20

N-Ethoxycarbonyl-2-[2-benzyloxy-4-(5-phenyl-2-pentyloxy)phenyl]-4-piperidone

Repeating the procedure of Example 1 but preparing the Grignard reagent with 2-benzyloxy-4-(5-phenyl-2-pentyloxy)bromobenzene, affords the title compound in like manner.

EXAMPLE 21

Similarly, the following products are prepared by the procedure of Example 1

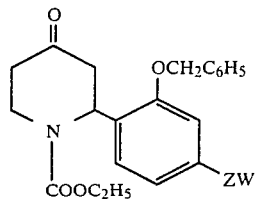

where Z and W are as defined below.

| Z | W |
|---|---|
| C(CH₃)₂(CH₂)₂ | H |
| C(CH₃)₂(CH₂)₁₀ | H |
| C(CH₃)₂(CH₂)₄ | C₆H₅ |
| C(CH₃)₂(CH₂)₄ | 4-pyridyl |
| C(CH₃)₂(CH₂)₃ | 2-pyridyl |
| C(CH₃)₂(CH₂)₁₀ | C₆H₅ |
| CH(CH₃)(CH₂)₂ | C₆H₅ |
| CH(C₂H₅)(CH₂)₂ | 4-ClC₆H₅ |
| CH(C₂H₅)(CH₂)₄ | 4-FC₆H₄ |
| (CH₂)₅ | H |
| CH₂ | C₆H₅ |
| (CH₂)₁₁ | H |
| (CH₂)₁₃ | H |
| (CH₂)₄ | C₆H₅ |
| (CH₂)₈ | H |
| O(CH₂)₄ | 4-FC₆H₄ |
| O(CH₂)₈ | C₆H₅ |
| O(CH₂)₁₀ | 4-ClC₆H₄ |
| OCH(CH₃)(CH₂)₈ | C₆H₅ |
| OCH(CH₃)CH₂ | 4-FC₆H₄ |
| OCH(CH₃)(CH₂)₃ | C₆H₅ |
| OCH₂CH(CH₃)CH₂ | C₆H₅ |
| OCH(CH₃)(CH₂)₁₀ | H |
| OC(CH₃)₂(CH₂)₅ | H |
| OC(CH₃)₂(CH₂)₇ | H |
| O(CH₂)₁₃ | H |
| O(CH₂)₁₃ | C₆H₅ |
| OCH(CH₃)(CH₂)₆ | 4-FC₆H₄ |
| OC(CH₃)₂(CH₂)₁₀ | 4-FC₆H₄ |
| O(CH₂)₁₂ | C₆H₅ |
| O(CH₂)₆ | C₆H₅ |
| O(CH₂)₂ | 4-pyridyl |
| OCH(CH₃)(CH₂)₃ | 2-pyridyl |
| O(CH₂)₅ | 3-pyridyl |
| O(CH₂)₁₀ | 2-pyridyl |
| OCH(C₂H₅)(CH₂)₂ | 4-pyridyl |

EXAMPLE 22

In like manner the following congeners are prepared by the procedure of Example 1 from the appropriate N-substituted-2,3-dihydro-4(1H)pyridinone and 2-benzyloxy-4-ZW-substituted bromobenzene.

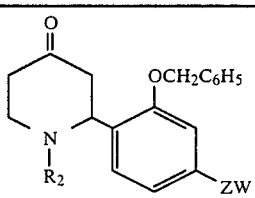

| R₂ | Z | W |
|---|---|---|
| CH₃ | C(CH₃)₂(CH₂)₆ | H |
| (CH₂)₂CH₃ | C(CH₃)₂(CH₂)₆ | H |
| CH₂CH(CH₃)₂ | C(CH₃)₂(CH₂)₆ | H |
| (CH₂)₄ | OCH(CH₃)(CH₂)₃ | C₆H₅ |
| CH₂CH(C₂H₅)₂ | OCH(CH₃)(CH₂)₃ | C₆H₅ |
| CH(CH₃)CH₂CH₃ | CH₂OCH₂ | H |
| (CH₂)₅CH₃ | CH₂O(CH₂)₄ | C₆H₅ |
| CH₂CH(CH₃)(CH₂)₂CH₃ | CH₂O(CH₂)₁₂ | 4-FC₆H₄ |

-continued

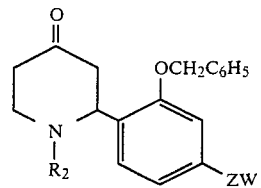

| R₂ | Z | W |
|---|---|---|
| CH=CH₂ | CH₂OCH₂CH(C₂H₅)CH₂ | 4-pyridyl |
| CH₂CH=CH₂ | CH₂)₂O(CH₂)₂ | H |
| CH₂CH=CHCH₃ | (CH₂)₃O(CH₂)₃ | H |
| (CH₂)₂CH=CH₂ | (CH₂)₃O(CH₂)₅ | H |
| CH₂CH=CH(CH₂)₂CH₃ | (CH₂)₅O(CH₂)₈ | H |
| CH₂CH=CH₂ | (CH₂)₆O(CH₂)₇ | C₆H₅ |
| C(CH₃)CH=CH₂ | CH(CH₃)(CH₂)₂O(CH₂)₄ | H |
| C(CH₃)CH=CHCH₃ | (CH₂)₆O | C₆H₅ |
| CH₂C(CH₃)=CH₂ | (CH₂)₁₃O | 2-pyridyl |
| (CH₂)₄CH=CH₂ | CH(CH₃)(CH₂)₂O | C₆H₅ |
| CH=CHCH₃ | (CH₂)₈O | 4-pyridyl |
| CH₃CO | (CH₂)₃O | 2-pyridyl |
| CH₃CH₂CO | (CH₂)₃OCH(CH₃) | C₆H₅ |
| CH₃(CH₂)₂CO | C(CH₃)₂(CH₂)₅ | H |
| (CH₃)₂CHCH₂CO | O(CH₂)₅ | 4-FC₆H₄ |
| CH₃(CH₂)₅CO | O(CH₂)₁₃ | C₆H₅ |
| (CH₃)₂CHCO | OCH(CH₃)(CH₂)₃ | C₆H₅ |
| (CH₃)₂C(CH₃)CO | OCH(CH₃)(CH₂)₃ | 4-ClC₆H₄ |
| (C₂H₅)₂CHCO | (CH₂)₄O(CH₂)₅ | 4-pyridyl |
| (C₂H₅)₂CHCH₂CO | (CH₂)₈O(CH₂)₅ | 4-pyridyl |
| HCO | CH₂ | H |
| CH₃OCO | CH₂ | C₆H₅ |
| C₂H₅OCO | OCH₂ | H |
| C₂H₅OCO | OCH₂ | C₆H₅ |
| CH₃OCO | (CH₂)₄OCH₂ | H |
| CH₃OCO | CH₂O(CH₂)₁₂ | H |
| n-C₃H₇OCO | CH₂OCH₂ | C₆H₅ |
| n-C₃H₇OCO | (CH₂)₂O(CH₂)₂ | H |
| i-C₄H₉OCO | C(CH₃)₂(CH₂)₆ | C₆H₅ |
| n-C₅H₁₁OCO | C(CH₃)₂(CH₂)₆ | H |
| n-C₆H₁₃OCO | OCH(CH₃)(CH₂)₃ | C₆H₅ |
| i-C₄H₉OCO | OCH(CH₃)(CH₂)₃ | 4-ClC₆H₄ |
| sec-C₅H₁₁OCO | (CH₂)₅ | H |

EXAMPLE 23

Sodium borohydride reduction of the 4-piperidones prepared in Examples 20-22 by the method of Example 2 similarly provides the corresponding 4-hydroxypiperidines of the formula below where R₁ is benzyl.

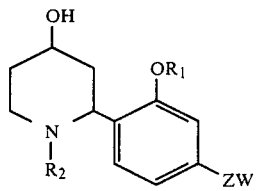

Catalytic hydrogenolysis employing a palladium catalyst and the method of Example 4 likewise provides the corresponding phenols where R₁ is hydrogen. In each case R₂, Z and W are as defined in Examples 20-22.

EXAMPLE 24 cis-2-[(5-phenyl-2-pentyloxy)-2-hydroxyphenyl]-4-piperidinol

Hydrolysis of N-ethoxycarbonyl-2-[2-benzyloxy-4-(5-phenyl-2-pentyloxy)phenyl]-4-piperidinol by the procedure of Example 3 and subsequent hydrogenolysis by the procedure of Example 4 provides the title compound in like manner.

Similarly the compounds of the formula below are obtained from the remaining N-alkoxycarbonyl compounds provided in Example 23

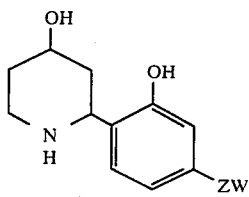

where Z and W are as defined in Examples 21 and 22.

EXAMPLE 25 cis-N-Methyl-2-[4-(5-phenyl-2-pentyloxy)-2-hydroxyphenyl]-4-piperidinol

Lithium aluminum hydride reduction of N-ethoxycarbonyl-2-[4-(5-phenyl-2-pentyloxy)-2-benzyloxyphenyl]-4-piperidone or the corresponding 4-piperidinol by the method described in Example 5 and debenzylation by the method of Example 6 provides the title compound.

In similar manner the compounds of the formula below are obtained

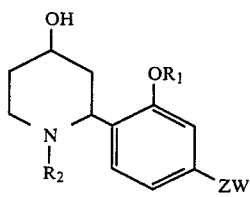

where $R_1$ is H or benzyl, $R_2$ is methyl and Z and W are as defined for the starting materials provided in Examples 21–23. In like manner the corresponding N-alkyl compounds [$R_2$=($C_2$–$C_6$)alkyl] are obtained when the alkanoylamides provided in Example 22 are employed as starting material.

EXAMPLE 26

N-Propyl-cis-2-[4-(5-phenyl-2-pentyloxy)-2-hydroxyphenyl]-4-piperidinol

Acylation of 2-[4-(5-phenyl-2-pentyloxy)-2-benzyloxyphenyl]-4-piperidinol with propionic anhydride by the method of Example 8, followed by lithium aluminum hydride reduction of the resulting N,O-dipropionyl intermediate by the method of Example 9, Part A, and finally, debenzylation by the method of Example 9, Part B, provides the title compound in like manner.

Similarly, the reaction of piperidinol bases provided in Examples 3 and 24 by the above reaction sequence, but employing the appropriate acid anhydride or acid chloride in place of propionic anhydride, provides the corresponding compounds as shown in the following reaction sequence:

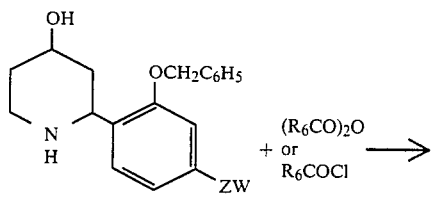

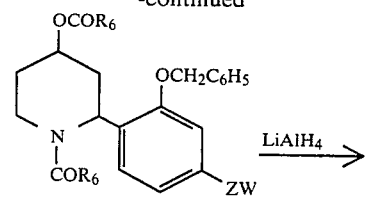

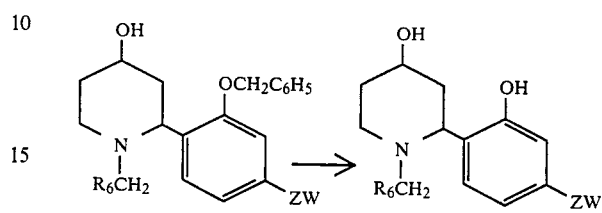

Z and W are as defined in Examples for the starting piperidinol and $R_6$ is an ($C_1$–$C_6$)alkyl residue.

EXAMPLE 27

N-Isobutyl-2-[2-hydroxy-4-(1,1-dimethylheptyl)-phenyl]piperidine

A.
N-Isobutyl-2-[2-benzyloxy-4-(1,1-dimethylheptyl)-phenyl]piperidine

A mixture of 2.32 g (5 mmoles) of N-isobutyl-2-[2-benzyloxy-4-(1,1-dimethylheptyl)phenyl]-4-piperidone, 10.2 ml hydrazine hydrate and 20 ml ethylene glycol is heated at 100° C. for one hour. The mixture is cooled to 60° C, and 4.05 g (72.3 mmoles) solid potassium hydroxide is added. After heating at 200° C. for two hours, the reaction mixture is cooled and added to 500 ml 1N hydrochloric acid and 300 ml ethyl ether. The ether layer is separated, washed with brine, sodium bicarbonate solution, dried over magnesium sulfate and the solvent evaporated at reduced pressure. The crude product is purified, if desired, by column chromatography on silica gel.

B. Debenzylation of the product obtained in Part A by the method of Example 4 provides the title compound.

C. In like manner the remaining N-alkyl piperidones and N-alkenylpiperidones provided in Example 22 are converted to the corresponding piperidine compounds of the formula

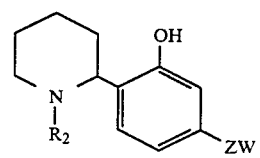

where $R_2$ is an alkyl or alkenyl residue as defined in Example 22.

EXAMPLE 28

Employing the appropriate alkenyl bromide, alkenyl chloride or alkenyl iodide and the appropriate 2-[2-benzyloxy-4-(ZW-substituted)phenyl]-4-piperidinol in the procedure of Example 10 provides the corresponding compound of the formula below where $R_1$ is benzyl. Removal of the benzyl group by the procedure of Example 4 yields the compound where $R_1$ is H. In each case $R_2$ is a $(C_2-C_6)$alkenyl group and Z and W are as defined in Example 22.

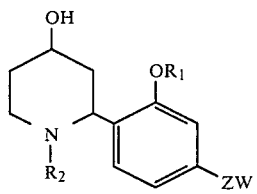

EXAMPLE 29

By means of the procedures of Examples 12 through 19, above, but employing the appropriate starting materials in each case, the following compounds are obtained in like manner.

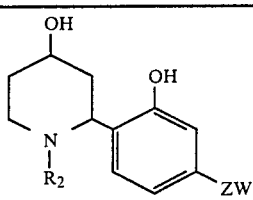

| $R_2$ | Z | W |
|---|---|---|
| $CH_3OCO$ | $CH_2$ | H |
| $C_2H_5OCO$ | $OCH_2$ | $C_6H_5$ |
| $CH_3OCO$ | $(CH_2)_4O(CH_2)_2$ | H |
| $n-C_3H_7OCO$ | $CH_2OCH_2$ | $C_6H_5$ |
| $i-C_4H_9OCO$ | $OCH_2(CH_3)(CH_2)_3$ | $4-ClC_6H_4$ |
| $n-C_6H_{13}OCO$ | $OCH(CH_3)(CH_2)_3$ | $C_6H_5$ |
| $C_2H_5OCO$ | $C(CH_3)_2(CH_2)_4$ | 4-pyridyl |
| $CH_3CH_2SO_2$ | $C(CH_3)_2(CH_2)_6$ | H |
| $CH_3SO_2$ | $OCH(CH_3)(CH_2)_3$ | $C_6H_5$ |
| $i-C_3H_7SO_2$ | $(CH_2)_{11}$ | H |
| $n-C_3H_7SO_2$ | $C(CH_3)_2(CH_2)_{10}$ | $C_6H_5$ |
| $n-C_4H_9SO_2$ | $O(CH_2)_4$ | $4-FC_6H_4$ |
| $i-C_4H_9SO_2$ | $CH_2OCH(CH_3)(CH_2)_4$ | 2-pyridyl |
| $sec-C_4H_9SO_2$ | $O(CH_2)_2$ | 4-pyridyl |
| $n-C_5H_{11}SO_2$ | $OCH(CH_3)(CH_2)_3$ | $C_6H_5$ |
| $(CH_3)_2CH(CH_2)_3SO_2$ | $OCH(CH_3)(CH_2)_3$ | $4-ClC_6H_4$ |
| $HOCH_2CO$ | $OCH(CH_3)(CH_2)_3$ | $C_6H_5$ |
| $HOCH_2CH_2$ | $OCH(CH_3)(CH_2)_3$ | $C_6H_5$ |
| $HO(CH_2)_2CO$ | $OCH(CH_3)(CH_2)_3$ | $C_6H_5$ |
| $HO(CH_2)_2CH_2$ | $OCH(CH_3)(CH_2)_3$ | $C_6H_5$ |
| $CH_3CH(OH)CO$ | $CH(CH_3)(CH_2)_4$ | H |
| $CH_3CH(OH)CH_2$ | $C(CH_3)_2(CH_2)_4$ | H |
| $HO(CH_2)_3CO$ | $C(CH_3)_2(CH_2)_4$ | H |
| $HO(CH_2)_3CH_2$ | $C(CH_3)_2(CH_2)_4$ | H |
| $HO(CH_2)_4CO$ | $OCH(CH_3)CH(CH_3)(CH_2)_4$ | $C_6H_5$ |
| $HO(CH_4)CH_2$ | $OCH(CH_3)CH(CH_3)(CH_2)_4$ | $C_6H_5$ |
| $CH_3CH_2CH(OH)CH_2CO$ | $(CH_2)_4O(CH_2)_4$ | 2-pyridyl |
| $CH_3CH_2CH(OH)CH_2CH_2$ | $(CH_2)_4O(CH_2)_4$ | 2-pyridyl |
| $CH_3(CH_2)_2CH(OH)CH_2CO$ | $(CH_2)_4O(CH_2)_9$ | H |
| $HO(CH_2)_6CO$ | $(CH_2)_9O(CH_2)_4$ | H |
| $HO(CH_2)_6CH_2$ | $(CH_2)_9O(CH_2)_4$ | H |
| $CH_3(CH_2)_4CH(OH)CO$ | $OCH(CH_3)(CH_2)_3$ | $C_6H_5$ |
| $CH_3(CH_2)_4CH(OH)CH_2$ | $OCH(CH_3)(CH_2)_3$ | $C_6H_5$ |
| CHO | $OCH(CH_3)(CH_2)_3$ | $C_6H_5$ |
| CHO | $(CH_2)_3O(CH_2)_3$ | H |
| $CH_3CO$ | $OCH(CH_3)(CH_2)_3$ | $C_6H_5$ |
| $CH_3CH_2CO$ | $(CH_2)_4O$ | $C_6H_5$ |
| $(CH_3)_2CHCO$ | $(CH_2)_3O$ | $4-ClC_6H_4$ |
| $CH_3(CH_2)_3CO$ | $OC(CH_3)_2(CH_2)_4$ | H |
| $HC\equiv CCO$ | $OCH(CH_3)(CH_2)_3$ | $C_6H_5$ |
| $HC\equiv CCH_2CO$ | $OCH(CH_3)(CH_2)_3$ | $C_6H_5$ |
| $CH_3C\equiv CCH_2CO$ | $OCH(CH_3)(CH_2)_3$ | $C_6H_5$ |
| $HC\equiv C(CH_2)_4CO$ | $C(CH_3)_2(CH_2)_6$ | H |
| $CH_3(CH_2)_3C\equiv CCO$ | $C(CH_3)_2(CH_2)_6$ | H |
| $CH_3CH_2C\equiv CCH_2CO$ | $OCH(CH_3)(CH_2)_3$ | $C_6H_5$ |
| $HC\equiv CCH_2$ | $OCH(CH_3)(CH_2)_3$ | $C_6H_5$ |
| $CH\equiv CCH_2$ | $(CH_2)_2O(CH_2)_4$ | H |
| $HC\equiv CCH_2$ | $CH(CH_3)(CH_2)_3O$ | $C_6H_5$ |
| $CH_3C\equiv CCH_2$ | $(CH_2)_4O$ | 4-pyridyl |

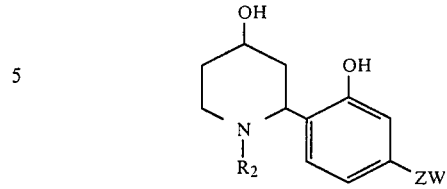

-continued

| $R_2$ | Z | W |
|---|---|---|
| $HC\equiv C$ | $(CH_2)_3O$ | 2-pyridyl |
| $HC\equiv C$ | $OCH(CH_3)(CH_2)_3$ | $C_6H_5$ |
| $CH_3CH_2C\equiv CCH_2$ | $OCH(CH_3)(CH_2)_3$ | $4-ClC_6H_5$ |
| $CH_3CHC\equiv C(CH_2)_2$ | $C(CH_3)_2(CH_2)_3$ | H |
| $CH_3(CH_2)_2C\equiv CCH_2$ | $C(CH_3)_2(CH_2)_3$ | 2-pyridyl |

EXAMPLE 30

N-n-Butyryl-2-[2-hydroxy-4-(5-phenyl-2-pentyloxy)phenyl]-4-piperidone

A. To a cooled solution of 25.8 g (50 mmol) N-n-butyryl-2-[benzyloxy-4-(5-phenyl-2-pentyloxy)phenyl]-4-piperidinol, 100 ml acetone, 6.0 g. (60 mmole) chromium trioxide, 15 ml water and 20 ml acetic acid is added dropwise 20 ml concentrated sulfuric acid at such a rate as to maintain the temperature at 5° C. The resulting mixture is stirred at 5°-20° C. for five hours, and then neutralized with ammonium hydroxide. The mixture is extracted with ethyl ether, the extracts washed with brine, dried (MgSO$_4$) and the solvent evaporated. The resulting crude material is purified by chromatography on silica gel to afford N-n-butyryl-2-[2-benzyloxy-4-(5-phenyl-2-pentyloxy)phenyl]-4-piperidone.

B. A mixture of 5 g of the benzyl ether obtained in Part A is dissolved in 100 ml ethanol and 100 ml ethyl acetate. To this is added 2 g of 10% palladium on carbon catalyst and the mixture is stirred under one atmosphere of hydrogen for 3 hours. The product is isolated and purified by the method of Example 4.

C. The remaining 4-piperidinols provided above are converted to the corresponding 4-piperidones of the formula below in like manner.

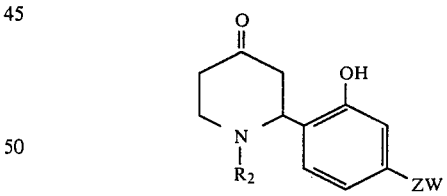

EXAMPLE 31

N-Propyl-2-[2-(4-N-piperidylbutyryloxy)-4-(1,1-dimethylheptyl)phenyl]-4-piperidinone Hydrochloride To a solution of 0.9 g (2.5 mmole) N-propyl-2-[2-hydroxy-4-(1,1-dimethylheptyl)phenyl]-4-piperidinone in 25 ml methylene chloride is added 0.52 g (2.5 mole) 4-piperidylbutyric acid hydrochloride, 0.573 g (2.78 mmole) dicyclohexylcarbodiimide and the mixture is stirred at room temperature for six hours. After holding overnight at 0° C., the mixture is filtered, the filtrate evaporated and the residue triturated with ethyl ether to afford the desired hydrochloride salt.

Alternatively, the filtrate is extracted with dilute hydrochloric acid. The aqueous phase washed with ether, neutralized with potassium hydroxide solution and extracted with ether. Evaporation affords the free base of the title compound.

Repetition of this procedure, but employing the appropriate phenol of the formula below where $R_1$ is H, and the appropriate carboxylic acid in place of 4-piperidylbutric acid hydrochloride provides the following compounds in like manner

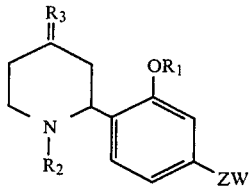

where $R_2$, $R_3$, Z and W are as defined above and $R_1$ is as shown below.

$R_1$ $COCH_2CH_3$
$CO(CH_2)_2CH_3$
$CO(CH_2)_3CH_3$
$COCH_2NH_2$
$CO(CH_2)_2NH_2$
$CO(CH_2)_4NH_2$
$CO(CH_2)N(CH_3)_2$
$CO(CH_2)_2NH(C_2H_5)$
$CO(CH_2)_4NHCH_3$
$CONH_2$
$CON(C_2H_5)_2$
$CON(C_4H_9)_2$
$CO(CH_2)_3NH(C_3H_7)$
$CO(CH_2)_2N(C_4H_9)_2$
$COCH_2$-piperidino
$COCH_2$-pyrrolo
$CO(CH_2)_2$-morpholino
$CO(CH_2)_2$-N-butylpiperazino
$CO(CH_2)_3$-pyrrolidino
CO-piperidino
CO-morpholino
CO-pyrrolo
CO—N-(methyl)piperazino
CO—$C_6H_5$
$COCH(CH_3)(CH_2)_2$-piperidino
CHO Basic esters are obtained as their hydrochloride salts. Careful neutralization with sodium hydroxide affords the free basic esters.

EXAMPLE 32

General Hydrochloride Acid Addition Salt Formation

Into an ethereal solution of the appropriate free base of formula (I), having one or more basic nitrogen containing groups, is passed a molar excess of anhydrous hydrogen chloride and the resulting precipitate is separated and recrystallized from an appropriate solvent, e.g. methanol-ether.

Similarly, the free bases of formula (I) are converted to their corresponding hydrobromide, sulfate, nitrate, phosphate, acetate, butyrate, citrate, malonate, maleate, fumarate, malate, glycolate, gluconate, lactate, salicylate, sulfosalicylate, succinate, pamoate and tartarate salts.

EXAMPLE 33

N-Butyryl-cis-2-[4-(1,1-dimethylheptyl)-2-hydroxyphenyl]-4-piperidinol, 100 mg, is intimately mixed and ground with 900 mg of starch. The mixture is then loaded into telescoping gelatin capsules such that each capsule contains 10 mg of drug and 90 mg of starch.

EXAMPLE 34

A tablet base is prepared by blending the ingredients listed below:

| | |
|---|---|
| Sucrose | 80.3 parts |
| Tapioca starch | 13.2 parts |
| Magnesium stearate | 6.5 parts |

N-Ethoxycarbonyl-cis-2-[4-(1,1-dimethylheptyl)-2-hydroxyphenyl]-4-piperidinol is blended into this base to provide tablets containing 0.1, 0.5, 1, 5, 10 and 25 mg of drug.

EXAMPLE 35

Suspensions of N-n-pentanoyl-cis-2-[4-(1,1-dimethylheptyl)-2-hydroxyphenyl]-4-piperidinol hydrochloride are prepared by adding sufficient amounts of drug to 0.5% methylcellulose to provide suspensions having 0.05, 0.1, 0.5, 1, 5 and 10 mg of drug per ml.

We claim:

1. A compound of the formula

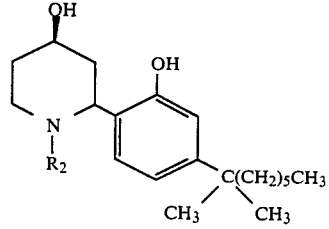

wherein $R_2$ is $COCH_2CH_2CH_3$ or $CO_2CH_2CH_3$.

2. The compound according to claim 1: N-butyryl cis-2-[4-(1,1-dimethylheptyl)-2-hyroxyphenyl]-4-piperidinol.

3. The compound according to claim 1: N-ethoxycarbonyl cis-2-[4-(1,1-dimethylheptyl)-2-hydroxyphenyl]-4-piperidinol.

4. A pharmaceutical composition suitable for use as an analgesic which comprises a pharmaceutically acceptable carrier and an analgesia-producing amount of a compound according to claim 1.

5. A method for producing analgesia in a mammalian subject which comprises orally or parenterally administering to said subject an analgesia producing amount of a compound according to claim 1.

* * * * *